United States Patent [19]
Pfister et al.

[11] 3,949,084
[45] Apr. 6, 1976

[54] NOVEL SUBSTITUTED XANTHONE CARBOXYLIC ACID COMPOUNDS

[75] Inventors: Jurg R. Pfister, Los Altos; Ian T. Harrison; John H. Fried, both of Palo Alto, all of Calif.

[73] Assignee: Syntex (U.S.A.) Inc., Palo Alto, Calif.

[22] Filed: Jan. 23, 1975

[21] Appl. No.: 543,390

Related U.S. Application Data

[63] Continuation-in-part of Ser. No. 231,756, March 3, 1972, abandoned.

[52] U.S. Cl. .............. 424/283; 424/251; 424/263; 424/269; 424/272; 424/274; 424/275
[51] Int. Cl.² ........................................ A61K 31/35
[58] Field of Search .................................. 424/283

[56] References Cited
UNITED STATES PATENTS

| | | | |
|---|---|---|---|
| 3,067,209 | 12/1962 | Doebel et al. | 260/335 |
| 3,073,847 | 1/1963 | Doebel et al. | 260/328 |
| 3,126,411 | 3/1964 | Bellet et al. | 260/570.8 |
| 3,467,623 | 9/1969 | Hinderer et al. | 260/47 |
| 3,642,997 | 2/1972 | Shen et al. | 424/250 |
| 3,678,077 | 7/1972 | Nakanishi et al. | 260/335 |
| 3,706,768 | 12/1972 | Bays | 424/283 |

FOREIGN PATENTS OR APPLICATIONS 773,649  5/1971  Belgium

*Primary Examiner*—Norman A. Drezin
*Attorney, Agent, or Firm*—Gerard A. Blaufarb; Walter H. Dreger; William B. Walker

[57] ABSTRACT

Compositions containing and methods employing, as the essential ingredient, novel substituted xanthone carboxylic acid compounds which are useful in the treatment of allergic conditions. Methods for preparing these compounds and compositions and intermediates therein are also disclosed. 6-Acetylxanthone-2-carboxylic acid is illustrated as a representative compound.

4 Claims, No Drawings

NOVEL SUBSTITUTED XANTHONE CARBOXYLIC ACID COMPOUNDS

This application is a continuation-in-part of application Ser. No. 231,756, filed Mar. 3, 1972, now abandoned.

The present invention is directed to novel substituted xanthone carboxylic acid compounds and to compositions containing and methods utilizing these compounds as the essential ingredient in the treatment of symptoms associated with allergic manifestations, for example, asthmatic conditions.

In a first aspect, the present invention relates to novel C-6 substituted xanthone-2-carboxylic acid compounds selected from those represented by the following formula:

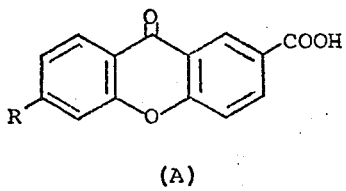

(A)

and the pharmaceutically acceptable, non-toxic esters, amides and salts thereof; wherein R is a group selected from those of the formulas

(wherein each of $R^1$ and $R^2$ is hydrogen; lower alkyl; cycloalkyl; halomethyl; phenyl; substituted phenyl, in which the substituent is halo, lower alkyl, lower alkoxy, lower alkylthio, trifluoromethyl, or cyano; or a monocyclic aromatic heterocyclic group having five or six total members, one or two of which are selected from nitrogen, oxygen, and sulfur), lower alkylsulfinyl, lower alkylsulfonyl, sulfo, sulfamoyl, monolower alkylsulfamoyl, or dilower alkylsulfamoyl.

Thus included within the scope of the present invention are

1. The C-6 1-hydroxyalkyl substituted xanthone-2-carboxylic acid compounds of the formula:

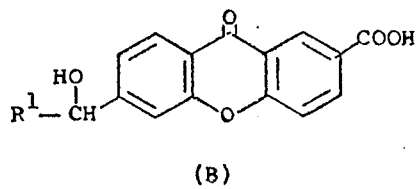

(B)

2. The C-6 acyl substituted xanthone-2-carboxylic acid compounds of the formula:

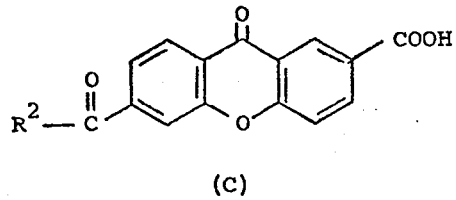

(C)

3. The C-6 lower alkylsulfinyl substituted xanthone-2-carboxylic acid compounds of the formula:

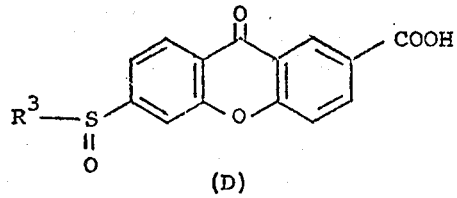

(D)

4. The C-6 lower alkylsulfonyl substituted xanthone-2-carboxylic acid compounds of the formula:

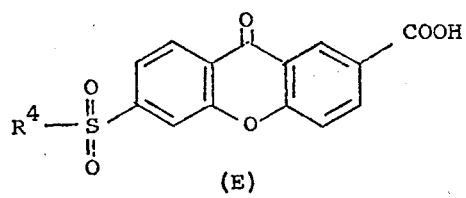

(E)

5. The C-6 sulfo substituted xanthone-2-carboxylic acid compounds of the formula:

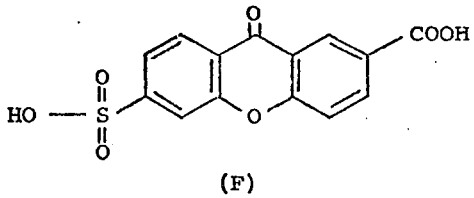

(F)

6. The C-6 sulfamoyl, N-monolower alkylsulfamoyl, and N,N-dilower alkylsulfamoyl substituted xanthone-2-carboxylic acid compounds of the formula:

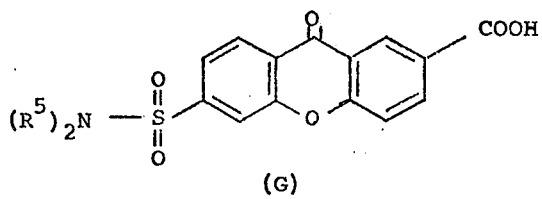

(G)

and the pharmaceutically acceptable, non-toxic esters, amides and salts thereof; wherein each of $R^1$ and $R^2$ is as above defined, each of $R^3$ and $R^4$ is lower alkyl, and each of $R^5$ is hydrogen, or lower alkyl.

In a second aspect, the present invention is directed to a method useful for relieving symptoms associated with allergic manifestations such as are brought about by antigen-antibody (allergic) reactions. In the relief of these symptoms, the method hereof serves to inhibit the effects of the allergic reaction when administered in an effective amount. While not intending to be bound by any theoretical mechanism of action, the method hereof is believed to operate by inhibiting the release and/or the action of toxic products, e.g., histamine, 5-hydroxytryptamine, slow releasing substance (SRS-A), and others, which are produced as a result of a combination of specific antibody and antigen (allergic reaction). These properties make the subject compounds particularly useful in the treatment of various allergic conditions.

This aspect of the present invention thus relates to a method useful for inhibiting the effects of the allergic reaction which comprises administering an effective amount of a compound selected from those represented by the above formula (A) or a pharmaceutically acceptable non-toxic composition incorporating said acids, esters, amides or salts as an essential ingredient.

The present invention, in a third aspect, is directed to pharmaceutical compositions useful for inhibiting the effects of the allergic reaction comprising an effective amount of a compound selected from those represented by the above formula (A) in admixture with a pharmaceutically acceptable non-toxic carrier.

In the practice of the method of the present invention, an effective amount of a compound of the present invention or pharmaceutical compositions thereof, as defined above, is administered via any of the usual and acceptable methods known in the art, either singly or in combination with another compound or compounds of the present invention or other pharmaceutical agents, such as antibiotics, hormonal agents, and so forth. These compounds or compositions can thus be administered orally, topically, parenterally, or by inhalation and in the form of either solid, liquid, or gaseous dosages including tablets, suspensions, and aerosols, as discussed in more detail hereinafter. The administration can be conducted in single unit dosage form with continuous therapy or in single dose therapy ad libitum, preferably prophylactically.

In view of the foregoing as well as in consideration of the degree of severity of the condition being treated, age of subject, and so forth, all of which factors being determinable by routine experimentation by one skilled in the art; the effective dosage in accordance herewith can vary over a wide range. Generally, an effective amount ranges from about 0.005 to about 100 mg. per kg. of body weight per day and preferably from about 0.01 to about 100 mg. per kg. of body weight per day. In alternate terms, an effective amount in accordance herewith generally ranges from about 0.5 to about 7000 mg. per day per subject.

Useful pharmaceutical carriers for the preparation of the compositions hereof, can be solids, liquids, or gases. Thus, the compositions can take the form of tablets, pills, capsules, powders, sustained release formulations, solutions, suspensions, elixirs, aerosols, and the like. The carriers can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like. Suitable pharmaceutical carriers and their formulation are described in "Remingtons Pharmaceutical Sciences" by E. W. Martin. Such compositions will, in any event, contain an effective amount of the active compound together with a suitable amount of carrier so as to prepare the proper dosage form for proper administration to the host.

The compounds of the present invention demonstrate activity as inhibitors of the effects of the allergic reaction as measured by tests indicative of such activity involving passive cutaneous anaphylaxis as substantially described, for example, by J. Goose et al., *Immunology*, 16, 749 (1969).

Certain of the compounds of the present invention can be prepared in accordance with the following reaction sequence:

Sequence A

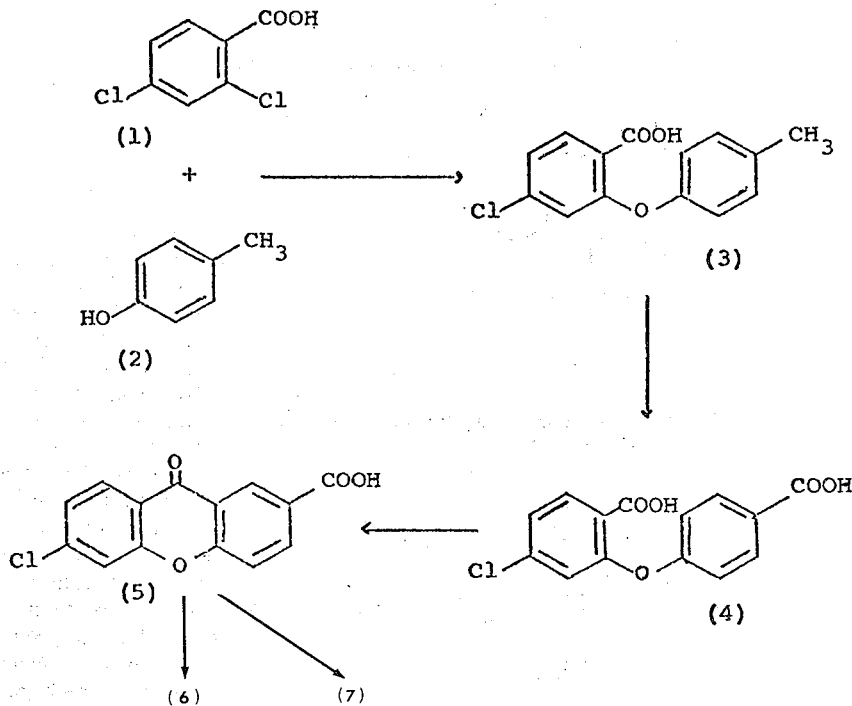

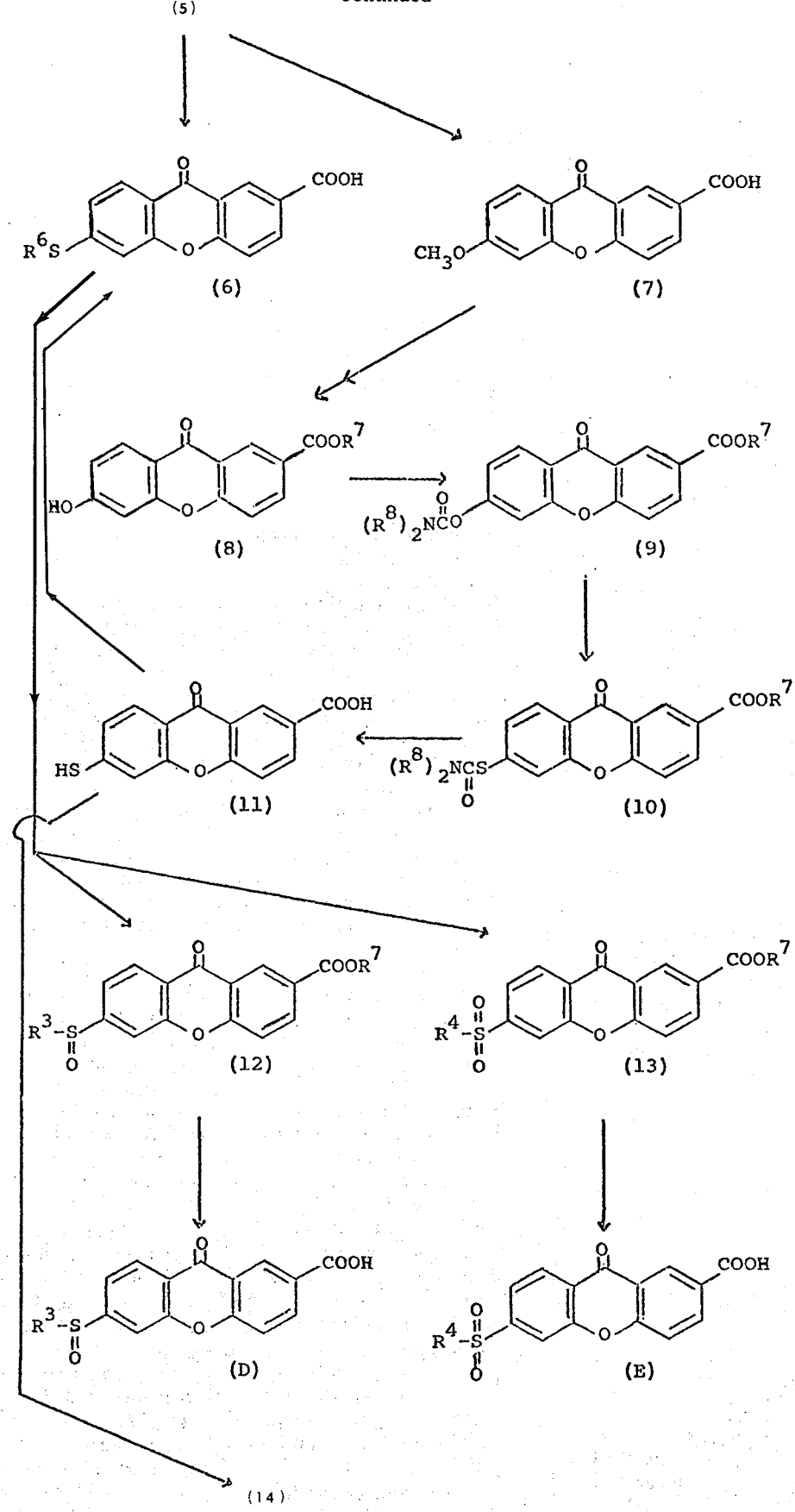

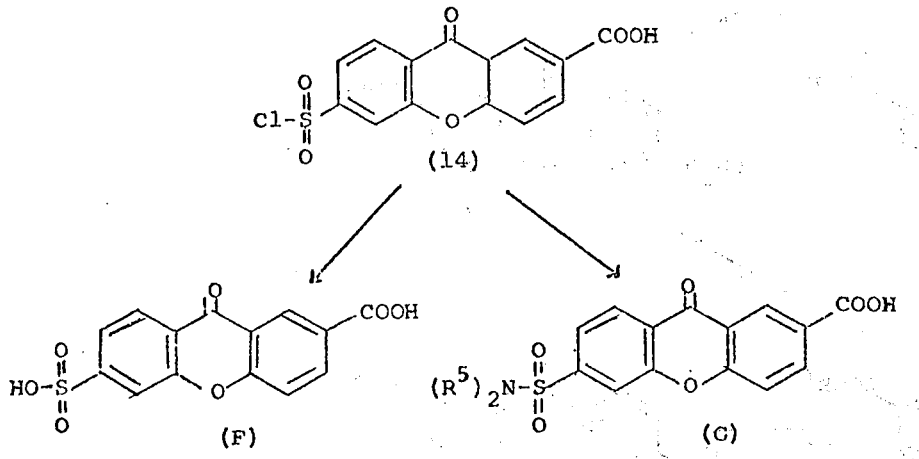

wherein
each of $R^3$, $R^4$, and $R^5$ is as above defined; and
each of $R^6$, $R^7$, and $R^8$ is lower alkyl, $R^7$ being preferably methyl.

With reference to the above reaction sequence, paramethyl phenol (2) is condensed with the 2,4-dichlorobenzoic acid (1) in the presence of copper powder with anhydrous potassium carbonate, optionally in organic liquid reaction medium, preferably an organic amide such as dimethyl acetamide, dimethylformamide, N-methylpyrrolidone, tetramethylurea, and so forth, to prepare the corresponding 2-(p-methylphenyloxy)-4-chlorobenzoic acid compound (3).

The reaction is preferably conducted in an inert organic reaction medium, such as those listed above, or suitable mixtures of one or more of such media. The reaction is further conducted at temperatures ranging from about 80° to about 220°C, preferably from about 120° to 200°C, and for a period of time sufficient to complete the reaction, ranging from about 2 hours to about 24 hours.

The reaction consumes the reactants on the basis of one mole of the substituted phenol per mole of the dichlorobenzoic acid. However, the amounts of the reactants to be employed are not critical, some of the desired compound (3) product being obtained when employing any proportions thereof. In the preferred embodiments, the reaction is conducted by reacting from about 1 to about 3 moles of the substituted phenol compound with about from 1 to about 1.2 moles of the dichlorobenzoic acid compound in the presence of catalytic amounts of the copper powder. The inert organic reaction medium, if employed, is used in solvent amounts.

Thereafter, the prepared compound (3) is oxidized with potassium permanganate in aqueous t-butanol to give the corresponding 2-(p-carboxyphenyloxy)-4-chlorobenzoic acid (4).

The thus-prepared diacid compound (4) is then cyclized with phosphoryl chloride, thionyl chloride, sulfuric acid, hydrogen fluoride, or, preferably, polyphosphoric acid (PPA), to give the corresponding 6-chloroxanthone-2-carboxylic acid compound (5). The reaction is preferably, but optionally, conducted in an inert organic reaction medium including those usually employed in organic chemical reactions, such as dimethylsulfoxide, sulfolane, benzene, toluene, and so forth. The reaction is further conducted at temperatures ranging from about 60° to about 180°C, and for a period of time sufficient to complete the reaction ranging from about 15 minutes to about 90 minutes.

Although the reaction consumes the reactants on the basis of one mole of compound (4) per mole of cyclizing reagent, the reaction can be performed using any proportions of reactants. In the preferred embodiments, however, the reaction is conducted using from about 20 to about 50 moles of the cyclizing reagent per mole of starting compound (4).

The 6-chloroxanthone-2-carboxylic acid (5) is then treated with excess alkali metal lower alkoxide, e.g., sodium methoxide to give compound (7) or with excess alkali metal thioloweralkoxide to give compounds (6). The reaction is preferably conducted in polar organic solvent at temperatures of from about 80° to about 150°C.

The 6-methoxyxanthone-2-carboxylic acid compound (7) thus prepared is converted to the respective 6-hydroxy compound by treatment with hydrobromic or hydroiodic acid and acetic acid. This reaction is conducted at a temperature of from about 100° to about 160°C followed by esterification ($R^7$) to give compounds (8). This reaction is conducted with ethereal diazoalkane such as diazomethane and diazoethane or with the desired lower alkyl iodide in the presence of lithium carbonate at room temperature or with the desired lower alkanol in the presence of a trace of sulfuric acid at reflux.

The hydroxy acid esters (8) are then treated with a dialkylthiocarbamoyl chloride, such as dimethylthiocarbamoyl chloride, in the presence of base, such as an alkali metal hydride, and in organic liquid reaction media, preferably an organic amide such as those listed above with respect to reaction (1 + 2 → 3) to afford the products (9). The reaction is conducted at temperatures ranging from about 20° to about 100°C, preferably from 60° to about 80°C and for a period of time sufficient to complete the reaction, ranging from about 1 hour to about 6 hours. In the preferred embodiments, the reaction is conducted by reaction of from about 1.1 to about 1.5 moles of dialkylthiocarbamoyl chloride per mole of compound (8).

The product compounds (9) are then rearranged by reaction at a temperature of from about 200° to about 250°C, preferably from about 220° to about 230°C, and for a period of time ranging from about 1 hour to about 8 hours and in the presence of organic medium such as sulfolane, nitrobenzene, triethyleneglycol, and so forth, which is preferably employed in solvent amounts, to give compound (10).

Compounds (10) are then converted to the corresponding 6-mercapto acid compounds (11) by base hydrolysis using an alkali metal hydroxide at about 50° to about 90°C and for a period of time sufficient to complete the reaction, ranging from about 15 minutes to about 60 minutes, preferably in the presence of inert organic reaction media such as those normally employed in organic chemical reactions of this type, e.g. aqueous alkanol solutions.

The 6-lower alkylthio ether, ester compounds can be prepared by reacting compounds (11) with a lower alkyl halide in the presence of base such as potassium carbonate and organic liquid reaction media such as those described above. The reaction is conducted at a temperature ranging from about 20° to about 80°C, preferably from 50° to about 60°C and for a period of time sufficient to complete the reaction, ranging from about 2 hours to about 16 hours. Hydrolysis of the ester, if desired, affords the 6-(lower alkylthio)-acid compounds (6).

Compound (6) is esterified to the acid ester, or the acid ester thereof prepared as described above, can be oxidized with a peracid, such as peracetic acid, m-chloroperbenzoic acid, p-nitroperbenzoic acid, perphthalic acid, and so forth, to give compounds (12) which can be hydrolyzed, as above described, to give the corresponding 6-lower alkylsulfinyl acid compounds (D). The oxidation is preferably conducted in liquid reaction media such as a chlorinated hydrocarbon, e.g. chloroform, methylene chloride, and carbon tetrachloride. The reaction is conducted at temperatures ranging from about 0° to about 60°C, preferably from 20° to about 30°C and for a period of time sufficient to complete the reaction, ranging from about 1 hour to about 6 hours. In the preferred embodiments, the reaction is conducted by reaction of from about 1 to about 1.1 moles of peracid.

Alternatively, the acid esters of compounds (6) are oxidized with excess hydrogen peroxide to give compounds (13) which can be hydroylzed as above described to give the 6-lower alkylsulfonyl acid compounds (E). The peroxide oxidation is preferably conducted in liquid reaction media such as a lower carboxylic acid, e.g. acetic acid and propionic acid. The reaction is further conducted at temperatures ranging from about 20° to about 100°C, preferably from 80° to about 90°C and for a period of time sufficient to complete the reaction, ranging from about 30 minutes to about 3 hours. In the preferred embodiments, the reaction is conducted by reaction of from about 5 to about 10 moles of hydrogen peroxide per mole of the esters of compound (6).

In said oxidation steps, and particularly that employing peracid, a mixture of products (12) and (13) may be obtained. If obtained, the mixture can be conventionally separated, such as via chromatography, if desired, to isolate the oxidized products.

The above oxidation steps can also be practiced on the acid starting compounds (6) to give respective products (D) or (E) without the need of a second hydrolysis step.

Alternatively, compounds (11) can be treated with excess chlorine under acidic conditions to afford compounds (14). This reaction is conducted employing a pH of about 1 by use of hydrochloric acid, optionally in acetic acid solution. The reaction is further conducted at temperatures ranging from about 20° to about 100°C, preferably from 50° to about 60°C and for a period of time sufficient to complete the reaction, ranging from about 2 hours to about 12 hours.

Compound (14) is then reacted with a base, such as alkali metal hydroxide, preferably under aqueous conditions and at a temperature ranging from about 20° to about 100°C, preferably from 80° to about 90°C and for a period of from about 1 hour to about 2 hours to give the 6-sulfo-substituted acid compounds (F).

Compounds (14) can be treated with ammonia, monolower alkylamine, or dilower alkylamine to give the 6-sulfamoyl, monolower alkylsulfamoyl, and dilower alkylsulfamoyl acid compounds (G). This reaction is conducted at temperatures ranging from about 0° to about 80°C, preferably from 20° to about 30°C, and for a period of time sufficient to complete the reaction, ranging from about 1 hour to about 8 hours. In the preferred embodiments, the reaction is conducted by reaction of from about 10 to about 20 moles of amine per mole of compound (14). This reaction is further conducted in organic reaction media such as those described above, preferably tetrahydrofuran, dioxane, dimethylsulfoxide, and so forth.

The 6-chlorosulfonylxanthone-2-carboxylic acid compound (14), as well as 6-mercaptoxanthone-2-carboxylic acid and the 6-lower alkylthioxanthone-2-carboxylic acid compounds hereof, are novel intermediates useful as described above.

Alternatively, certain of the compounds of the present invention can be prepared in accordance with the following:

Sequence B

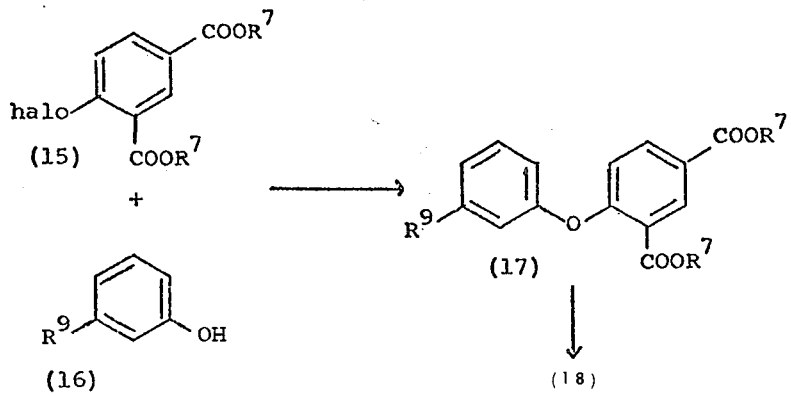

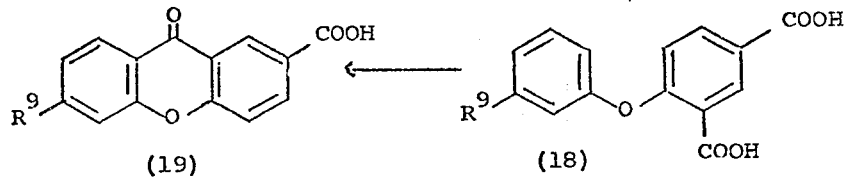

wherein
R⁹ is lower alkylthio, or chloro;
R⁷ is as defined above; and
halo is bromo, chloro, fluoro, or iodo, preferably bromo.

With reference to above Sequence B, the phenols (16) are condensed with compound (15), as above described, to give the adducts (17). These compounds are then hydrolyzed (i.e. 10 → 11 in Sequence A) to give the diacid compounds (18) which are cyclized as described above to compounds (19). The products are useful as described and depicted by Sequence A.

Certain compounds hereof are prepared as illustrated by the following sequence:

Sequence C

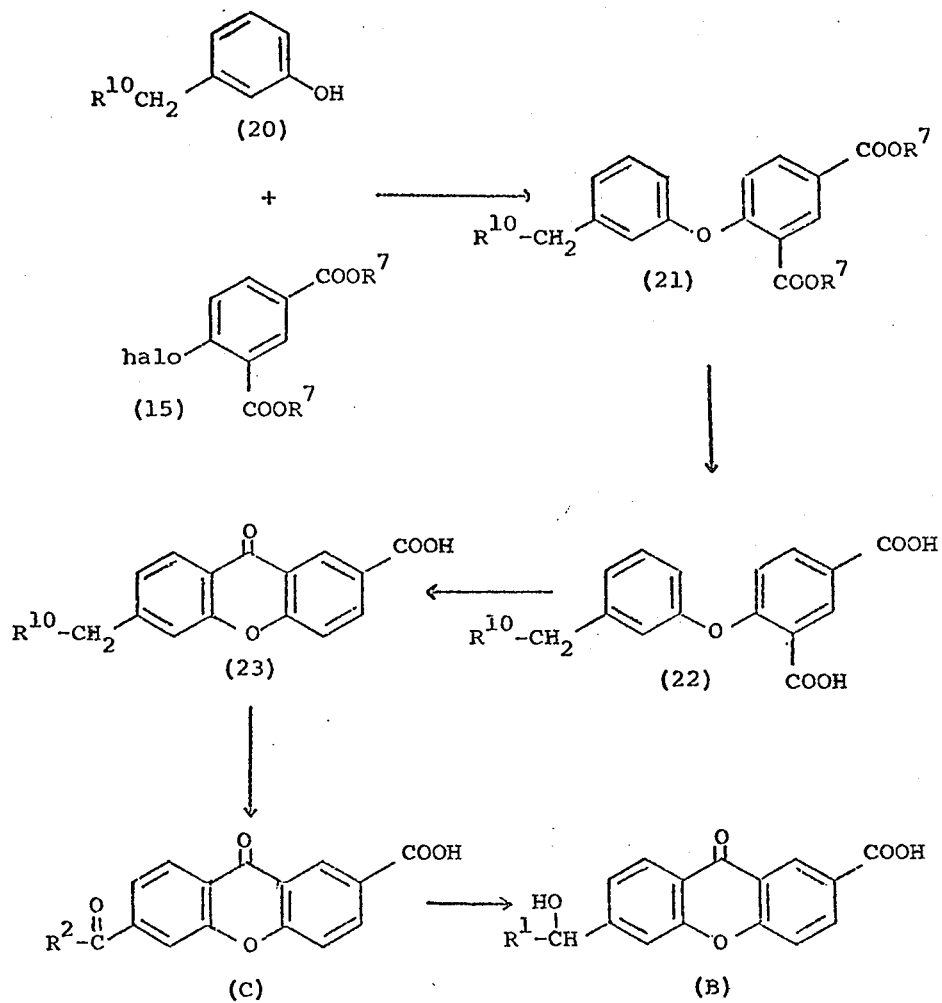

wherein
R[10] is lower alkyl; and
each of R[1], R[2], R[7], and halo is as above defined.

With reference to the above reaction sequence, the 6-substituted-xanthone-2-carboxylic compounds (23) are prepared following the above reaction Sequence B (15 + 16 → → 17 → 18 → 19) with the respective starting compounds (20). The resultant compounds (23), or their esters, are oxidized with chromium trioxde in acetic acid-acetic anhydride to give the 6-acyl compounds (C) which are reduced with sodium borohydride to give the 6-(secondary hydroxyalkyl)-xanthone-2-carboxylic acid products (D). Alternative to the above procedure, the 6-substituted xanthone-2-carboxylic acid (23) can be converted to its corresponding ester and it treated with N-bromosuccinimide to prepare the corresponding 6-(substituted bromomethyl) compound (i.e., 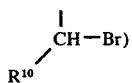)

which can be converted to the corresponding alcohol upon treatment with aqueous base, to give the product acids (B).

Certain of the compounds hereof can be prepared as follows:

Sequence D

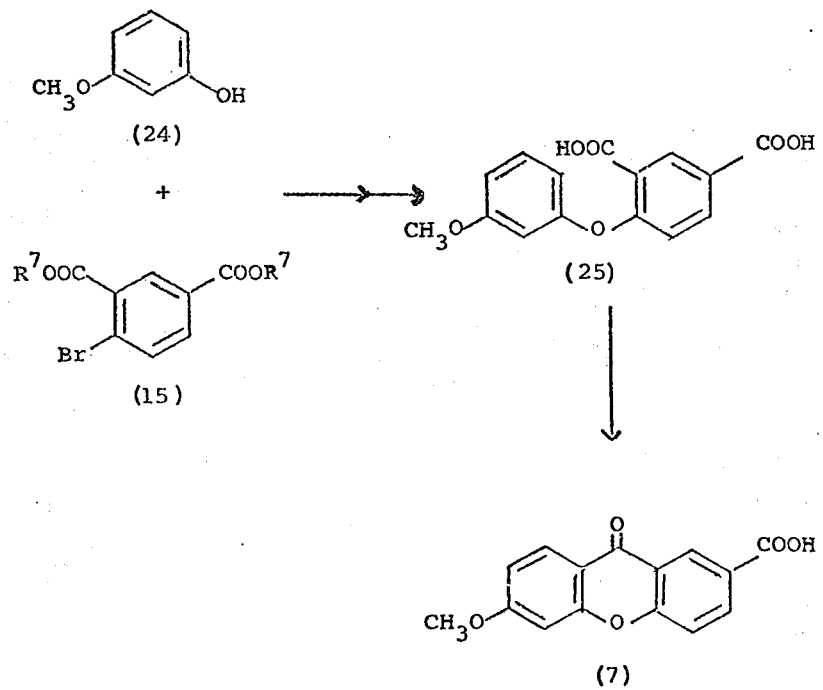

wherein R[7] is as defined above.

In the above Sequence, compounds (24) and (15) are condensed as described above, e.g. 1 + 2 → 3, to give the diacid compound (25) which is cyclized as described above, e.g. 4 → 5, to give compound (7) which is useful as depicted and described in Sequence A above.

An alternative method for the preparation of certain of the compounds hereof is represented as follows:

Sequence E

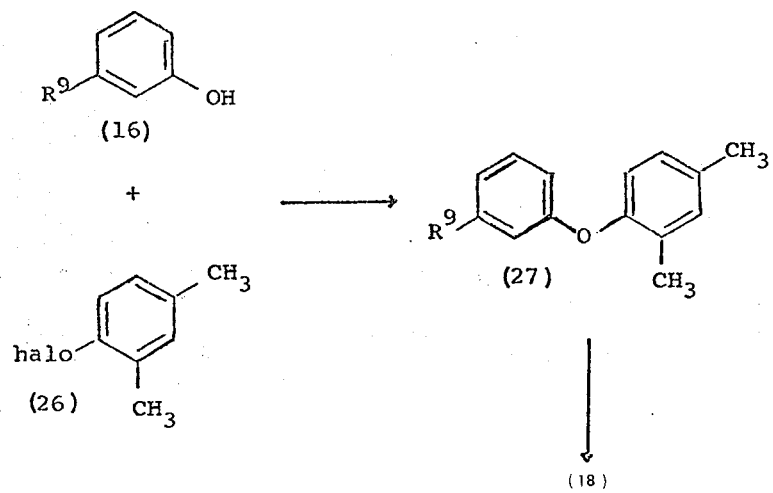

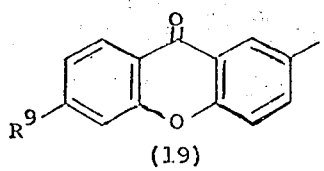 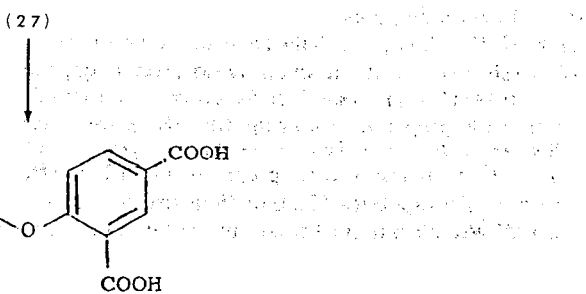

wherein R⁹ and halo are as defined above.

With reference to Sequence E, an appropriate phenol (16) is treated with 1,3-dimethyl-4-halo-(preferably iodo)-benzene (26), as described above, to prepare the corresponding 1,3-dimethyl-4-phenyloxybenzene (27). This compound is then oxidized such as with potassium permanganate in aqueous t-butanol, as described above, e.g. 3 → 4, to give (18) which is then cyclized, as described above, to give the corresponding xanthone-2-carboxylic acid (19) useful as described above to prepare the compounds of the present invention.

Certain of the compounds hereof in the 6-hydroxyalkyl and 6-acyl series can be prepared by treating acetanilide with an appropriate acid chloride, e.g. benzoyl chloride, to give the corresponding p-acylacetanilide compound, converting the latter with dilute mineral acid to p-acylaniline. The latter is treated with bromine to give the corresponding o-bromo-p-acylaniline which, when treated with sodium nitrite and sodium fluoroborate followed by treatment with nickel carbonyl, gives the corresponding o-bromo-p-acylbenzoic acid. The latter is esterified and reacted with p-hydroxybenzoate followed by hydrolysis and cyclization, all as described above, to give the 6-acylxanthone-2-carboxylic acid compounds. Reduction of the acyl group, as described above, affords the corresponing 6-hydroxyalkyl compounds.

The acid esters of the xanthone-2-carboxylic acids hereof are prepared as described above upon treatment of the acid with ethereal diazoalkane such as diazomethane and diazoethane or with the desired lower alkyl iodide in the presence of lithium carbonate at room temperature or with the desired lower alkanol in the presence of a trace of sulfuric acid at reflux. The glycerol esters are prepared by treating the acid with thionyl chloride followed by treatment with a suitably protected ethylene glycol or propylene glycol (e.g. solketal) in pyridine, and hydrolyzing the protecting group of the ester thus formed with dilute acid.

The amides of the xanthone-2-carboxylic acids hereof are prepared by treatment of the acids with thionyl chloride followed by treatment with anhydrous ammonia, alkyl amine, dialkyl amine, dialkylaminoalkylamine, alkoxyalkylamine, or phenethylamine.

The salts of the xanthone-2-carboxylic acids hereof are prepared by treating the corresponding acids with a pharmaceutically acceptable base. Representative salts derived from such pharmaceutically acceptable bases include the sodium, potassium, lithium, ammonia, calcium, magnesium, ferrous, ferric, zinc, manganous, aluminum, manganic, trimethylamine, triethylamine, tripropylamine, β-(dimethylamino)-ethanol, triethanolamine, β-(diethylamino)ethanol, arginine, lysine, histidine, N-ethylpiperidine, hydrabamine, choline, betaine, ethylenediamine, glucosamine, methyl glucamine, theobromine, purines, piperazine, piperidine, polyamine resins, caffeine, procaine salts. The reaction is conducted in an aqueous solution, alone or in combination with an inert, water-miscible organic solvent, at a temperature of from about 0°C to about 100°C, preferably at room temperature. Typical inert, water-miscible organic solvents include methanol, ethanol, isopropanol, butanol, acetone, dioxane, or tetrahydrofuran. When divalent metal salts are prepared, such as the calcium salts or magnesium salts of the acids, the free acid starting material is treated with about one-half molar equivalent of pharmaceutically acceptable base. When the aluminum salts of the acids are prepared, about one-third molar equivalent of the pharmaceutically acceptable base is employed.

In the preferred embodiment of the present invention, the calcium salts and magnesium salts of the acids are prepared by treating the corresponding sodium or potassium salts of the acids with at least one-half molar equivalent of calcium chloride or magnesium chloride, respectively, in an aqueous solution, alone or in combination with an inert water-miscible organic solvent, at a temperature of from about 20°C to about 100°C.

In the preferred embodiment of the present invention, the aluminum salts of the acids are prepared by treating the acids with at least one-third molar equivalent of an aluminum alkoxide, such as aluminum triethoxide, aluminum tripropoxide, and the like, in a hydrocarbon solvent, such as benzene, xylene, cyclohexane, and the like, at a temperature of from 20°C to about 115°C.

In the sulfo series, use of one equivalent of base provides the sulfo acid monosalts; use of two equivalents provides the disalts.

The starting compounds for use in the present invention are known and can be prepared in accordance with known procedures. Thus, the 1,3-dicarbo(lower)alkoxy-4-halobenzene starting compounds are conveniently prepared by oxidizing 1,3-dimethyl-4-halobenzene (4-halo-m-xylene) with potassium permanganate, as described above, followed by conventional esterification. Lower alkoxyphenylcarboxylic acid chloride acylating agents for the preparation of alkoxyphenylcarbonylacetanilide starting compounds, are prepared, for example, by selectively esterifying hydroxybenzoic acid with methanol and a trace of sulfuric acid or with lithium carbonate and methyl halide in dimethylformamide. The resultant hydroxybenzoate ester is then conventionally alkylated with lower alkylhalide and potassium carbonate followed by selective hydrolysis of the ester of the carboxylic acid group and conversion to the acid chloride with, e.g. thionyl chloride.

In the present specification and claims, by the term "lower alkyl" is intended a lower alkyl group containing 1 to 8 carbon atoms including straight and branched chain groups, for example, methyl, ethyl, n-propyl, isopropyl, n-butyl, isobutyl, sec-butyl, t-butyl, n-pentyl, isopentyl, sec-pentyl, t-pentyl, n-hexyl, n-pentyl, n-octyl, isooctyl. The term "cycloalkyl" includes cyclopropyl, cyclobutyl, cyclopentyl, and cyclohexyl. By the term "lower alkoxy" is intended the group "O-lower alkyl" wherein "lower alkyl" is as defined above. By the term "lower alkylthio" is intended the group "S-lower alkyl" wherein "lower alkyl" is as defined above. The term "substituted phenyl" includes p-substituted phenyl. The term "monocyclic aromatic heterocyclic group" includes pyridyl, pyridazinyl, pyrimidinyl, pyrazinyl, pyrazolyl, imidozolyl, furanyl, thiophenyl, pyrrolyl, isoxazolyl, and oxazolyl. By the term "halomethyl" is meant trifluoromethyl, trichloromethyl, difluoromethyl, and dichloromethyl.

By the term "pharmaceutically acceptable, non-toxic esters, amides, and salts" is respectively intended an alkyl or glycerol ester; an unsubstituted, monoalkyl, dialkyl, dialkylaminoalkyl, alkoxyalkyl, or phenethyl substituted amide and a salt as defined above.

In the hydroxyalkyl and alkylsulfinyl series the compounds may possess a chiral center. The methods hereof generate each of the d and l and dl forms and each is thus included within the scope hereof. If desired, the isomers can be separated by conventional means such as forming the alkaloid salts of the products and employing fractional crystallization.

The nomenclature herein is employed in accordance with *Chemical Abstracts*, 56, Subject Index (1962, January – June).

The following examples illustrate the method by which the present invention can be practiced.

EXAMPLE 1

A mixture of 15 g. of 2,4-dichlorobenzoic acid, 10 g. of p-methylphenol, 0.5 g. of copper powder and 20 g. of anhydrous potassium carbonate in 200 ml. of dimethylformamide is heated to 165°C and maintained thereat with stirring and under a nitrogen atmosphere. After monitoring via tlc indicates the reaction is substantially complete, the reaction mixture is diluted with water, treated with charcoal, filtered and the clear filtrate acidified. The precipitate is isolated by suction filtration, washed neutral and dried to give 2-(p-methylphenyloxy)-4-chlorobenzoic acid.

A mixture of 12 g. of 2-(p-methylphenyloxy)-4-chlorobenzoic acid, 72 g. of potassium permanganate, 200 ml. of t-butanol and 350 ml. of water is refluxed for 4.5 hours. After this time, the t-butanol is distilled off, and the reaction mixture is filtered. The filtrate is acidified to give 2-(p-carboxyphenyloxy)-4-chlorobenzoic acid which can be recrystallized from benzene:heptane.

Two g. of 2-(p-carboxyphenyloxy)-4-chlorobenzoic acid in 20 ml. of concentrated sulfuric acid is stirred at 80°C for 1 hour. After this time, the reaction mixture is poured into 200 ml. of ice water and the resultant mixture is heated on a steam bath for 15 minutes. The mixture is cooled and filtered with the precipitate being washed with water and then recrystallized from acetic acid to give 6-chloroxanthone-2-carboxylic acid.

EXAMPLE 2

6-Chloroxanthone-2-carboxylic acid (2.5 g.) and 1.8 g. of sodium methyl mercaptide in 40 ml. of hexamethylphosphoramide (HMPA) is stirred for 2 hours at 100°C. After acidification, the product is filtered off, washed with water and dried to give 6-(methylthio)-xanthone-2-carboxylic acid.

In like manner, the following compounds can be prepared:
6-(ethylthio)-xanthone-2-carboxylic acid,
6-(n-propylthio)-xanthone-2-carboxylic acid,
6-(isopropylthio)-xanthone-2-carboxylic acid,
6-(n-buthylthio)-xanthone-2-carboxylic acid,
6-(isobutylthio)-xanthone-2-carboxylic acid,
6-(sec-butylthio)-xanthone-2-carboxylic acid,
6-(t-butylthio)-xanthone-2-carboxylic acid,
6-(pentylthio)-xanthone-2-carboxylic acid,
6-(cyclopropylthio)-xanthone-2-carboxylic acid,
6-(cyclobutylthio)-xanthone-2-carboxylic acid, and
6-(cyclopentylthio)-xanthone-2-carboxylic acid.

The compound 6-methoxyxanthone2-carboxylic acid is prepared by employing sodium methoxide in the above procedure.

EXAMPLE 3

A mixture of 11 g. of 6-methoxyxanthone-2-carboxylic acid in 100 ml. of concentrated aqueous hydrogen iodide and 100 ml. of acetic acid is refluxed for 4 hours. After this time, the mixture is cooled, diluted with water, and filtered. The precipitate is washed and dried to give 6-hydroxyxanthone-2-carboxylic acid.

EXAMPLE 4

A mixture of 4 g. of 6-hydroxyxanthone-2-carboxylic acid, 10 g. of methyl iodide, and 10 g. of lithium carbonate in 50 ml. of dimethylformamide is stirred at room temperature for a period of 16 hours. After this period of time, the reaction mixture is poured into dilute hydrochloric acid-ice and the resultant mixture extracted with ethyl acetate. The extracts are filtered through alumina to give methyl 6-hydroxyxanthone-2-carboxylate which can be recrystallized from methanol.

EXAMPLE 5

To a solution of 6.2 g. of methyl 6-hydroxyxanthone-2-carboxylate in 100 ml. of dimethylformamide are added 1 g. of sodium hydride. The mixture is stirred for 10 minutes at room temperature under nitrogen. Dimethylthiocarbamoyl chloride (3 g.) is then added thereto and the resultant mixture stirred at 70°C for 6 hours and then at room temperature for 16 hours. The mixture is then poured into 200 ml. of water containing 1 ml. of acetic acid; the resultant mixture is filtered and the solid dried to give methyl 6-dimethylthiocarbamoyloxyxanthone-2-carboxylate.

Methyl 6-dimethylthiocarbamoyloxyxanthone-2-carboxylate (8 g.) in 150 ml. of sulfolane is stirred at 230°C under nitrogen. After a total of 6 hours under these conditions, tlc indicates the absence of starting material. The mixture is cooled to 80°C and 150 ml. of hot water are slowly added. The mixture is then cooled and the filtered solid washed with water and dried to give methyl 6-(dimethylcarbamoylthio)-xanthone-2-carboxylate.

Methyl 6-(dimethylcarbamoylthio)-xanthone-2-carboxylate (7.5 g.), 10 g. of potassium hydroxide and 250 ml. of 80% aqueous ethanol is refluxed for 1 hour. After this time, 250 ml. of water are added and the mixture is treated with charcoal, filtered, acidified. The product is filtered off and dried to give 6-mercaptoxanthone-2-carboxylic acid.

EXAMPLE 6

A mixture of 3 g. of 6-mercaptoxanthone-2-carboxylic acid in 150 ml. of dimethylformamide, 5 ml. of methyl iodide and 5 ml. of potassium carbonate is stirred for 16 hours at 60°C. The mixture is then poured into dilute hydrochloric acid and the resultant mixture extracted with ethyl acetate. The extracts are chromatographed on alumina (methylene chloride) to give methyl 6-(methylthio)-xanthone-2-carboxylate (i.e. methyl 6-thiomethoxyxanthone-2-carboxylate) which can be recrystallized from methylene chloride:methanol.

A mixture of 580 mg. of methyl 6-(methylthio)-xanthone-2-carboxylate, 30 ml. of ethanol, 5 ml. of saturated sodium carbonate solution and 5 ml. of water is refluxed for 1 hour. The mixture is then cooled, acidified and the precipitate filtered off to give 6-(methylthio)-xanthone-2-carboxylic acid (i.e. 6-thiomethoxyxanthone-2-carboxylic acid) as also prepared in the alternative method described in Example 2.

A mixture of 0.8 g. of 6-mercaptoxanthone-2-carboxylic acid, 2 ml. of 2-bromopropane, and excess potassium carbonate in 50 ml. of dimethylformamide is stirred for 24 hours at 75°C. Dilute hydrochloric acid and ethanol are added, the solid filtered off and washed. The solid is saponified with sodium carbonate in aqueous methanol (30 minutes reflux). The alkaline solution is diluted with water, treated with charcoal, filtered, and acidified to give 6-(isopropylthio)-xanthone-2-carboxylic acid which can be recrystallized from tetrahydrofuran:ethyl acetate.

In a similar manner (and alternative to the method of Example 2), the following are prepared from the respective starting compounds:
  6-(ethylthio)-xanthone-2-carboxylic acid,
  6-(n-propylthio)-xanthone-2-carboxylic acid,
  6-(n-butylthio)-xanthone-2-carboxylic acid,
  6-(sec-butylthio)-xanthone-2-carboxylic acid,
  6-(isobutylthio)-xanthone-2-carboxylic acid,
  6-(t-butylthio)-xanthone-2-carboxylic acid,
  6-(n-pentylthio)-xanthone-2-carboxylic acid,
  6-(cyclopropylthio)-xanthone-2-carboxylic acid,
  6-(cyclobutylthio)-xanthone-2-carboxylic acid, and
  6-(cyclopentylthio)-xanthone-2-carboxylic acid.

EXAMPLE 7

Methyl 6-(methylthio)-xanthone-2-carboxylate (764 mg.), 2 ml. of hydrogen peroxide (30%), and 40 ml. of acetic acid are heated on the steam bath (80°C) for 90 minutes. Tlc indicates the absence of starting material. The mixture is diluted with 60 ml. of hot water, and the mixture is cooled, the solid is filtered off and dried to give methyl 6-methylsulfonylxanthone-2-carboxylate which can be recrystallized from acetic acid:water.

Methyl 6-methylsulfonylxanthone-2-carboxylate (660 mg.), 1 g. of potassium hydroxide, and 60 ml. of 80% aqueous ethanol are refluxed for 30 minutes. The mixture is filtered, acidified, and the solid filtered off to give 6-methysulfonylxanthone-2-carboxylic acid.

Likewise, from the respective starting compounds are prepared the following compounds:
  6-isopropylsulfonylxanthone-2-carboxylic acid,
  6-ethylsulfonylxanthone-2-carboxylic acid,
  6-n-propylsulfonylxanthone-2-carboxylic acid,
  6-n-butylsulfonylxanthone-2-carboxylic acid,
  6-sec-butylsulfonylxanthone-2-carboxylic acid,
  6-isobutylsulfonylxanthone-2-carboxylic acid,
  6-t-butylsulfonylxanthone-2-carboxylic acid,
  6-n-pentylsulfonylxanthone-2-carboxylic acid,
  6-cyclopropylsulfonylxanthone-2-carboxylic acid,
  6-cyclobutylsulfonylxanthone-2-carboxylic acid, and
  6-cyclopentylsulfonylxanthone-2-carboxylic acid.

EXAMPLE 8

Methyl 6-(methylthio)-xanthone-2-carboxylate (927 mg.) in 60 ml. of methylene chloride is cooled to 0°C (ice). m-Chloroperbenzoic acid (555 mg.) is then added and the mixture is stirred at 0°C for 75 minutes. The reaction mixture is then filtered through alumina and the column washed with methylene chloride to give methyl 6-methylsulfinylxanthone-2-carboxylate which can be recrystallized from benzene:heptane.

Methyl 6-methylsulfinylxanthone-2-carboxylate (720 mg.), 75 ml. of ethanol, and 10 ml. of 5% sodium hydroxide are refluxed for 30 minutes. The mixture is cooled, partially evaporated and acidified. The precipitate is filtered off, washed and dried to give 6-methylsulfinylxanthone-2-carboxylic acid which can be recrystallized from acetic acid.

Likewise, from the respective starting compounds are prepared the following compounds:
  6-isopropylsulfinylxanthone-2-carboxylic acid,
  6-ethylsulfinylxanthone-2-carboxylic acid,
  6-n-propylsulfinylxanthone-2-carboxylic acid,
  6-n-butylsulfinylxanthone-2-carboxylic acid,
  6-sec-butylsulfinylxanthone-2-carboxylic acid,
  6-isobutylsulfinylxanthone-2-carboxylic acid,
  6-t-butylsulfinylxanthone-2-carboxylic acid,
  6-n-pentylsulfinylxanthone-2-carboxylic acid,
  6-cyclopropylsulfinylxanthone-2-carboxylic acid,
  6-cyclobutylsulfinylxanthone-2-carboxylic acid, and
  6-cyclopentylsulfinylxanthone-2-carboxylic acid.

The procedures of Examples 7 and 8 can be practiced upon the corresponding acid starting compounds to give the same products without the need of the hydrolysis step.

EXAMPLE 9

One g. of 6-mercaptoxanthone-2-carboxylic acid is dissolved in 30 ml. of acetic acid containing 3 ml. of concentrated hydrochloric acid under warming. The solution is then saturated with chlorine gas and stirred at room temperature overnight. The solution is then diluted with water and the precipitate filtered off, washed, and dried to give 6-chlorosulfonlyxanthone-2-carboxylic acid.

The thus-prepared chlorosulfonyl compound is then treated with aqueous potassium hydroxide to give 6-sulfoxanthone-2-carboxylic acid.

EXAMPLE 10

A mixture of 1 g. of 6-chlorosulfonylxanthone-2-carboxylic acid, 2 ml. of concentrated aqueous ammonia, and 20 ml. of dioxane is stirred at room temperature overnight. The mixture is then diluted with water, acidified and the solid filtered off and dried to give 6-sulfamoylxanthone-2-carboxylic acid.

Upon substituting a primary amine, such as methylamine and ethylamine, or a secondary amine, such as dimethylamine and diethylamine, for ammonia in the above method, the corresponding C-6 N-monolower alkylsulfamoyl and N,N-dilower alkylsulfamoyl products are obtained, e.g.:

6-methylsulfamoylxanthone-2-carboxylic acid,
6-ethylsulfamoylxanthone-2-carboxylic acid,
6-n-propylsulfamoylxanthone-2-carboxylic acid,
6-isopropylsulfamoylxanthone-2-carboxylic acid,
6-dimethylsulfamoylxanthone-2-carboxylic acid,
6-diethylsulfamoylxanthone-2-carboxylic acid,
6-di-n-propylsulfamoylxanthone-2-carboxylic acid,
6-di-isopropylsulfamoylxanthone-2-carboxylic acid,
and so forth.

EXAMPLE 11

1,3-Dicarbomethoxy-4-bromobenzene and m-methylthiophenol are condensed by the procedure of Example 1, paragraph 1, to give 1,3-dicarbomethoxy-4-(m-methylthiophenyloxy)-benzene. This compound is hydrolyzed with a 5% potassium hydroxide:methanol solution at reflux for 1 hour to give 1,3-dicarboxy-4-(m-methylthiophenyloxy)-benzene. The resultant compound is cyclized according to the procedure of Example 1, paragraph 3, to give 6-(methylthio)-xanthone-2-carboxylic acid.

In like manner, the other 6-(lower alkylthio)-xanthone-2-carboxylic acids and 6-chloroxanthone-2-carboxylic acid are prepared from the appropriate starting compounds.

The thus-prepared compounds are useful as described above in Examples 2, 7, and 8.

EXAMPLE 12

6-Lower alkylxanthone-2-carboxylic compounds are prepared in accordance with the procedures of Example 11 from m-lower alkylphenol starting compounds. Thus prepared, for example, are:

6-ethylxanthone-2-carboxylic acid,
6-n-propylxanthone-2-carboxylic acid,
6-n-butylxanthone-2-carboxylic acid,
6-isobutylxanthone-2-carboxylic acid,
6-n-pentylxanthone-2-carboxylic acid,
6-isopentylxanthone-2-carboxylic acid,
6-sec-pentylxanthone-2-carboxylic acid,
6-t-pentylxanthone-2-carboxylic acid,
6-n-hexylxanthone-2-carboxylic acid,
6-cyclopropylmethylxanthone-2-carboxylic acid,
6-cyclobutylmethylxanthone-2-carboxylic acid, and
6-cyclopentylmethylxanthone-2-carboxylic acid.

The methyl esters thereof are prepared as described in Example 4.

EXAMPLE 13

A mixture of 4 g. of 6-ethylxanthone-2-carboxylic acid, 10 g. of methyl iodide, and 10 g. of potassium carbonate in 50 ml. of dimethylformamide is stirred at room temperature for a period of 16 hours. After this period of time, the reaction mixture is poured into dilute hydrochloric acidice and the resultant mixture extracted with ethyl acetate. The extracts are filtered through alumina to give methyl 6-ethylxanthone-2-carboxylate which can be recrystallized from methanol.

A suspension of 2.5 g. of methyl 6-ethylxanthone-2-carboxylate and 2.5 g. of chromic oxide in 190 ml. of acetic acid and 10 ml. of acetic anhydride is stirred at room temperature for a period of 6 hours. After monitoring the reaction by tlc indicates the absence of starting material, 10 ml. of isopropanol are added and the resultant mixture warmed on the steam bath. Water (200 ml.) is then added portionwise to the resultant mixture which is cooled to room temperature. The precipitate is filtered off, washed, and dried to obtain methyl 6-acetylxanthone-2-carboxylate.

A mixture of 1.09 g. of methyl 6-acetylxanthone-2-carboxylate, 70 ml. of isopropanol, 5 ml. of saturated sodium carbonate solution, and 25 ml. of water is refluxed for 2 hours. The resultant mixture is then acidified, cooled and the crystals filtered off, washed, and dried to give 6-acethylxanthone-2-carboxylic acid.

The foregoing procedures can be followed with other 6-substituted methyl compounds (prepared according to the procedures of Example 12) to give the corresponding 6-acyl compounds, to wit:

6-propionylxanthone-2-carboxylic acid,
6-n-butyrylxanthone-2-carboxylic acid,
6-isobutyrylxanthone-2-carboxylic acid,
6-n-pentanoylxanthone-2-carboxylic acid,
6-isopentanoylxanthone-2-carboxylic acid,
6-sec-pentanoylxanthone-2-carboxylic acid,
6-t-pentanoylxanthone-2-carboxylic acid,
6-n-hexanoylxanthone-2-carboxylic acid,
6-cyclopropylcarbonylxanthone-2-carboxylic acid,
6-cyclobutylcarbonylxanthone-2-carboxylic acid, and
6-cyclopentylcarbonylxanthone-2-carboxylic acid.

EXAMPLE 14

A mixture of 1.077 g. of methyl 6-acetylxanthone-2-carboxylate, 200 mg. of sodium borohydride and 150 ml. of tetrahydrofuran is stirred for 2.5 hours at room temperature. The reaction is monitored by tlc. After this period of time, a 5% aqueous acetic acid solution is added to the reaction mixture dropwise to neutrality and the resultant solution evaporated under vacuum and crystallized by the addition of ethanol and hot water. The precipitate is filtered off, washed and dried to give methyl 6-(1-hydroxyethyl)-xanthone-2-carboxylate.

A mixture of 860 mg. of methyl 6-(1-hydroxyethyl)-xanthone-2-carboxylate, 60 ml. of ethanol and 2 ml. of 2N sodium hydroxide is refluxed for 30 minutes. The resultant mixture is cooled, acidified and the precipitate is filtered off, washed, and dried to give 6-(1-hydroxyethyl)-xanthone-2-carboxylic acid.

The foregoing procedures are practiced upon the other 6-acyl methyl esters prepared as described in Example 13 to give the following products, through their respective methyl esters:
  6-(1-hydroxy-n-propyl)-xanthone-2-carboxylic acid,
  6-(1-hydroxy-n-butyl)-xanthone-2-carboxylic acid,
  6-(1-hydroxy-isobutyl)-xanthone-2-carboxylic acid,
  6-(1-hydroxy-n-pentyl)-xanthone-2-carboxylic acid,
  6-(1-hydroxy-isopentyl)-xanthone-2-carboxylic acid,
  6-(1-hydroxy-sec-pentyl)-xanthone-2-carboxylic acid,
  6-(1-hydroxy-t-pentyl)-xanthone-2-carboxylic acid,
  6-(1-hydroxy-n-hexyl)-xanthone-2-carboxylic acid,
  6-((cyclopropyl)hydroxymethyl)-xanthone-2-carboxylic acid,
  6-((cyclobutyl)hydroxymethyl)-xanthone-2-carboxylic acid, and
  6-((cyclopentyl)hydroxymethyl)-xanthone-2-carboxylic acid.

EXAMPLE 15 m-Methoxyphenol and the methyl diester of 4-bromo-1,3-dicarboxy benzene are condensed and hydrolyzed to 4-(m-methoxyphenyloxy)-1,3-dicarboxybenzene according to the procedure of Example 1. This compound is then cyclized (Example 1, paragraph 3) to give 6-methoxyxanthone-2-carboxylic acid which is useful as described in Example 3 et seq.

EXAMPLE 16

A mixture of 51.5 g. of 1,3-dimethyl-4-iodobenzene (4-iodo-m-xylene), 40 g. of m-methylthiophenol, 16 g. of cuprous oxide in 300 ml. of dimethylacetamide is heated to the boiling point and maintained under reflux (190°C) for 144 hours with stirring and under a nitrogen atmosphere. The reaction mixture is then poured into ice water and extracted with ether and the extracts are filtered through 500 g. of alumina in hexane to give 1,3-dimethyl-4-(m-chlorophenyloxy)-benzene.

A mixture of 41 g. of 1,3-dimethyl-4-(m-chlorophenyloxy)-benzene, 300 g. of potassium permanganate, 500 ml. of t-butanol, and 750 ml. of water is heated to the boiling point and maintained thereat for a period of three hours. After distilling off the t-butanol, the reaction mixture is filtered, the clear filtrate acidified and the precipitate of 1,3-dicarboxy-4-(m-chlorophenyloxy)-benzene is isolated by suction filtration and washed with water.

The 1,3-dicarboxy-4-(m-chlorophenyloxy)-benzene thus prepared is then cyclized as described in Example 1 or 17 to give 6-(chloroxanthone-2-carboxylic acid.

EXAMPLE 17

A mixture of 1,3-dimethyl-4-bromobenzene, 10.5 g. of m-methoxyphenol, 4.65 g. of cuprous oxide, 40 ml. of tetramethylurea, and 75 ml. of N-methylpyrrolidone is stirred at 165° for 96 hours. The resultant mixture is diluted with water and extracted with methylene chloride. The methylene chloride extracts are chromatographed on 300 g. of alumina with gradient elution using hexane:ether to give 1,3-dimethyl-4-(m-methoxyphenyloxy)-benzene.

A mixture of 12 g. of 1,3-dimethyl-4-(m-methoxyphenyloxy)-benzene, 72 g. of potassium permanganate, 200 ml. of t-butanol and 350 ml. of water is refluxed for 4½ hours. After this time, the t-butanol is distilled off, and the reaction mixture is filtered. The filtrate is acidified to give 1,3-dicarboxy-4-(m-methoxyphenyloxy)-benzene which can be recrystallized from benzene:heptane.

A mixture of 3 g. of 1,3-dicarboxy-4-(m-methoxyphenyloxy)-benzene, 75 ml. of polyphosphoric acid, and 75 ml. of sulfolane is stirred at 125°C for a period of 2 hours. After this time, the reaction mixture is poured into water, filtered and the precipitate washed. The precipitate is recrystallized from acetic acid (charcoal) to give 6-methoxyxanthone-2-carboxylic acid which can be converted to 5-hydroxyxanthone-2-carboxylic acid.

In a similar manner, the foregoing porcedure can be practiced utilizing other m-lower alkoxyphenol starting compounds to prepare the corresponding products, for example,
  6-ethoxyxanthone-2-carboxylic acid,
  6-n-propoxyxanthone-2-carboxylic acid,
  6-isopropoxyxanthone-2-carboxylic acid,
  6-n-butoxyxanthone-2-carboxylic acid, and so forth,
which can each be converted to 5-hyroxyxanthone-2-carboxylic acid.

EXAMPLE 18

An ice-cooled solution of 5 grams of acetanilide and 15 g. of aluminum chloride in 75 ml. of dichloroethane is treated with 5 g. of benzoyl chloride in portions. The mixture is then heated at 80°C for 3 hours, decomposed with ice and dilute hydrochloric acid and the resulting solid isolated by suction filtration and recrystallized from ethanol:water to give p-benzoylacetanilide.

p-Benzoylacetanilide (2.8 g.) and 100 ml. of 1N hydrochloric acid are refluxed for six hours. After cooling, the solution is made alkaline by the addition of 2N sodium hydroxide solution and extracted with ether to give 4-aminobenzophenone, which is recrystallized from methanol.

Bromine (5.5 g.) is added dropwise to a stirred solution of 6.75 g. of 4-aminobenzophenone in 120 ml. of chloroform. After the addition is complete, stirring is continued for 30 minutes. Dilute sodium bicarbonate solution is added and the mixture is extracted with chloroform. The resulting bromo derivative can be recrystallized from methanol.

4-Amino-3-bromobenzophenone (11.4 g.) is suspended in a hot mixture of 10 ml. of concentrated hydrochloric acid and 10 ml. of water. After cooling the mixture to 0°C, a solution of 3.0 g. of sodium nitrite in 10 ml. of water is added dropwise. To the resulting clear solution of the diazonium chloride, a solution of 6 g. of sodium fluoroborate in 10 ml. of water is added with vigorous stirring. The precipitate is isolated by suction filtration, washed successively with 5% fluroboric acid, methanol, and ether and left to dry in the air.

Acetic acid (15 ml.) is added dropwise to a cooled solution of 2.5 g. of the diazonium fluroborate in 25 ml. nickel carbonyl. The mixture is then concentrated in vacuo and diluted with water. The precipitated 4-benzoyl-2-bromobenzoic acid is collected on a sintered glass filter and recrystallized from ethanol.

The resultant compound is esterified as described in Example 4 and then reacted with methyl p-hydroxybenzoate as described in Example 16, first paragraph, followed by hydrolysis (Example 5, last paragraph) and cyclization (Example 1, last paragraph) to give 6-benzoylxanthone-2-carboxylic acid. The later can be reduced (Example 14, first paragraph) to give 6-((phenyl)hydroxymethyl)-xanthone-2-carboxylic acid.

In like manner, the following are prepared:
  6-propionylxanthone-2-carboxylic acid;
  6-n-butyrylxanthone-2-carboxylic acid;

6-isobutyrylxanthone-2-carboxylic acid;
6-n-pentanoylxanthone-2-carboxylic acid;
6-isopentanoylxanthone-2-carboxylic acid;
6-sec-pentanoylxanthone-2-carboxylic acid;
6-t-pentanoylxanthone-2-carboxylic acid;
6-n-hexanoylxanthone-2-carboxylic acid;
6-n-heptanoylxanthone-2-carboxylic acid;
6-n-octanoylxanthone-2-carboxylic acid;
6-n-nonanoylxanthone-2-carboxylic acid;
6-cyclopropylcarbonylxanthone-2-carboxylic acid;
6-cyclobutylcarbonylxanthone-2-carboxylic acid;
6-cyclopentylcarbonylxanthone-2-carboxylic acid;
6-cyclohexylcarbonylxanthone-2-carboxylic acid;
6-trifluoroacetylxanthone-2-carboxylic acid;
6-difluoroacetylxanthone-2-carboxylic acid;
6-trichloroacetylxanthone-2-carboxylic acid;
6-dichloroacetylxanthone-2-carboxylic acid;
6-(p-chlorobenzoyl)-xanthone-2-carboxylic acid;
6-(p-methylbenzoyl)-xanthone-2-carboxylic acid;
6-(p-methoxybenzoyl)-xanthone-2-carboxylic acid;
6-(p-thiomethoxybenzoyl)-xanthone-2-carboxylic acid;
6-furoylxanthone-2-carboxylic acid;
6-pyrroylxanthone-2-carboxylic acid;
6-thenoylxanthone-2-carboxylic acid;
6-pyridylcarbonylxanthone-2-carboxylic acid;
6-imidazolylcarbonylxanthone-2-carboxylic acid; and
6-oxazolylcarbonylxanthone-2-carboxylic acid; and thence:
6-(1-hydroxy-n-propyl)-xanthone-2-carboxylic acid;
6-(1-hydroxy-n-butyl)-xanthone-2-carboxylic acid;
6-(1-hydroxyisobutyl)-xanthone-2-carboxylic acid;
6-(1-hydroxy-n-pentyl)-xanthone-2-carboxylic acid;
6-(1-hydroxyisopentyl)-xanthone-2-carboxylic acid;
6-(1-hydroxy-sec-pentyl)-xanthone-2-carboxylic acid;
6-(1-hydroxy-t-pentyl)-xanthone-2-carboxylic acid;
6-(1-hydroxy-n-hexyl)-xanthone-2-carboxylic acid;
6-(1-hydroxy-n-heptyl)-xanthone-2-carboxylic acid;
6-(1-hydroxy-n-octyl)-xanthone-2-carboxylic acid;
6-(1-hydroxy-n-nonyl)-xanthone-2-carboxylic acid;
6-((cyclopropyl)hydroxymethyl)-xanthone-2-carboxylic acid;
6-((cyclobutyl)hydroxymethyl)-xanthone-2-carboxylic acid;
6-((cyclopentyl)hydroxymethyl)-xanthone-2-carboxylic acid;
6-((cyclohexyl)hydroxymethyl)-xanthone-2-carboxylic acid;
6-(2,2,2-trifluoro-1-hydroxyethyl)-xanthone-2-carboxylic acid;
6-(2,2-difluoro-1-hydroxyethyl)-xanthone-2-carboxylic acid;
6-(2,2,2-trichloro-1-hydroxyethyl)-xanthone-2-carboxylic acid;
6-(-dichloro--dichloro-1-hydroxyethyl)-xanthone-2-carboxylic acid;
6-((p-chlorophenyl)hydroxymethyl)-xanthone-2-carboxylic acid;
6-((p-methylphenyl)hydroxymethyl)-xanthone-2-carboxylic acid;
6-((p-methoxyphenyl)hydroxymethyl)-xanthone-2-carboxylic acid;
6-((p-thiomethoxyphenyl)hydroxymethyl)-xanthone-2-carboxylic acid;
6-((furyl)hydroxymethyl)-xanthone-2-carboxylic acid;
6-((pyrryl)hydroxymethyl)-xanthone-2-carboxylic acid;
6-((thienyl)hydroxymethyl)-xanthone-2-carboxylic acid;
6-((pyridyl)hydroxymethyl)-xanthone-2-carboxylic acid;
6-((imioazolyl)hydroxymethyl)-xanthone2-carboxylic acid; and
6-((oxazolyl)hydroxymethyl)-xanthone-2-carboxylic acid.

EXAMPLE 19

Methyl 6-methylxanthone-2-carboxylate is prepared by the procedure of Example 11 from m-methylphenol.

To a solution of 2.4 g. of methyl 6-methylxanthone-2-carboxylate in 30 ml. acetic acid and 30 ml. acetic anhydride are added 4.8 ml. concentrated sulfuric acid at 0°C. After the addition of 5.6 g. of chromic acid, the mixture is stirred for 5 hours. The crude diacetoxymethyl intermediate is isolated by diluting the reaction mixture with water and filtering off the precipitate. The formyl derivative is obtained by refluxing the diacetoxymethyl compound thus obtained with 10 ml. 2N sulfuric acid in 90 ml. methanol for 30 minutes, cooling, diluting with 60 ml. water and filtering off the precipitate to give 6-formylxanthone-2-carboxylic acid. This compound can be reduced as described above to 6-hydroxymethylxanthone-2-carboxylic acid.

EXAMPLE 20

A mixture of 4.5 grams of 6-methylsulfinylxanthone-2-carboxylic acid, 10 g. of methyl iodide, and 10 g. of lithium carbonate in 75 ml. of dimethylformamide is stirred at room temperature for a period of 18 hours. After this period of time, the reaction mixture is poured into dilute hydrochloric acid-ice and the resultant precipitate is filtered off and washed to give methyl 6-methylsulfinylxanthone-2-carboxylate.

The foregoing procedure is repeated using the alternate lower alkyl iodides so as to prepare the corresponding lower alkyl acid esters hereof, e.g.
ethyl 6-methylsulfinylxanthone-2-carboxylate,
n-propyl 6-methylsulfinylxanthone-2-carboxylate,
isopropyl 6-methylsulfinylxanthone-2-carboxylate,
n-propyl 6-methylsulfinylxanthone-2-carboxylate,
isobutyl 6-methylsulfinylxanthone-2-carboxylate,
sec-butyl 6-methylsulfinylxanthone-2-carboxylate,
t-butyl 6-methylsulfinylxanthone-2-carboxylate,
n-pentyl 6-methylsulfinylxanthone-2-carboxylate, and so forth.

In like manner, the other xanthone-2-carboxylic acids hereof containing substituents at the C-6 position, prepared as described above, can be converted to the corresponding acid esters, e.g. methyl 6-methylsulfonylxanthone-2-carboxylate, ethyl 6-methylsulfonylxanthone-2-carboxylic acid, n-propyl 6-sulfamoylxanthone-2-carboxylic acid, and so forth.

In the sulfo series, the esters are prepared by treating the acid with the appropriate lower alkanol under reflux and in the absence of acid to give, e.g. methyl 6-sulfoxanthone-2-carboxylic acid and ethyl 6-sulfoxanthone-2-carboxylic acid.

EXAMPLE 21

To a solution of 10 g. of 6-methylsulfinylxanthone-2-carboxylic acid in 200 ml. of ethanol is added the theoretical amount of sodium hydroxide dissolved in 200 ml. of 90% ethanol. The reaction mixture is then concentrated in vacuum to give sodium 6-methylsulfinylxanthone-2-carboxylate.

In a similar manner, the potassium and lithium salts are prepared. Similarly, by replacing the sodium salt by means of an appropriate metal salt reagent, e.g. calcium chloride, manganese chloride, and so forth, the other xanthone-2-carboxylic acid salts are prepared, e.g.

magnesium 6-methylsulfinylxanthone-2-carboxylate,
calcium 6-methylsulfinylxanthone-2-carboxylate,
aluminum 6-methylsulfinylxanthone-2-carboxylate,
ferrous 6-methylsulfinylxanthone-2-carboxylate,
zinc 6-methylsulfinylxanthone-2-carboxylate,
manganese 6-methylsulfinylxanthone-2-carboxylate,
ferric 6-methylsulfinylxanthone-2-carboxylate, and so forth.

In a similar manner, the xanthone-2-carboxylic acid salts of the other C-6 substituted xanthone-2-carboxylic acids hereof are prepared, e.g. potassium 6-methylsulfonylxanthone-2-carboxylate, sodium 6-sulfamoylxanthone-2-carboxylate, and so forth.

In the sulfo series, use of one equivalent of base provides the sulfo acid salt and use of two or more equivalents provides the disalt, e.g. 6-sulfoxanthone-2-carboxylic acid disodium salt.

EXAMPLE 22

To a mixture of 50 ml. of concentrated aqueous ammonia in 500 ml. of methanol there are added 20 g. of 6-sulfamoylxanthone-2-carboxylic acid. The resultant mixture is stirred for two hours and is then evaporated to dryness to give the ammonium salt of 6-sulfamoylxanthone-2-carboxylic acid.

A solution of 10 g. of 6-sulfamoylxanthone-2-carboxylic acid in 50 ml. of thionyl chloride is heated at reflux for 1 hour. Thereafter, the solution is evaporated to dryness to give the corresponding acid chloride to which is added a concentrated ethereal ammonia solution. The resultant solution is evaporated giving the 6-sulfamoylxanthone-2-carboxylic acid amide.

In like manner, the lower alkyl amides can be prepared using monoalkylamine or dialkylamine in lieu of ammonia in the above procedures. Thus prepared, e.g. are:

6-methylsulfamoylxanthone-2-carboxylic acid amide,
N-methyl 6-n-propylsulfinylxanthone-2-carboxylic acid amide,
N,N-dimethyl 6-dimethylsulfamoylxanthone-2-carboxylic acid amide,
N,N-diethyl 6-ethylsulfonylxanthone-2-carboxylic acid amide,
N-ethyl 6-sulfoxanthone-2-carboxylic acid amide,
N-n-propyl 6-propylsulfinylxanthone-2-carboxylic acid amide, and so forth.

EXAMPLE 23

To a mixture of 20 g. of procaine and 500 ml. of aqueous methanol are added 20 g. of 6-methylsulfinylxanthone-2-carboxylic acid. The resultant mixture is stirred at room temperature for 16 hours. It is then evaporated under reduced pressure, to give the procaine salt of 6-methylsulfinylxanthone-2-carboxylic acid.

Similarly, the lysine, caffeine, and arginine salts thereof are obtained. In like manner, the e.g. procaine, lysine, caffeine, and arginine salts of the other 6-substituted xanthone-2-carboxylic acids are obtained, e.g. the procaine salt of 6-ethylsulfonylxanthone-2-carboxylic acid, the caffeine salt of 6-propylsulfinylxanthone-2-carboxylic acid, the lysine salt of 6-di-t-butyl sulfamoylxanthone-2-carboxylic acid, the procaine salt of 6-sec-butylsulfinylxanthone-2-carboxylic acid, and the arginine salt of 6-sulfoxanthone-2-carboxylic acid.

EXAMPLE 24

The following procedures illustrate the method by which the pharmaceutical compositions of the compounds hereof are prepared.

Sodium chloride (0.44 g.) is dissolved in 80 ml. of a (9.47 g/l. water) sodium hydrogen phosphate solution. A sodium dihydrogen phosphate (8.00 g/l. water) solution (20 ml.) is then added thereto. The resultant solution having a pH of 7.38 is sterilized in an autoclave. This vehicle is then added to solid, dry 6-methylsulfinylxanthone-2-carboxylic acid to give a preparation suitable for intravenous injection containing 2.5 mg. of 6-methylsulfinylxanthone-2-carboxylic acid per ml. of total composition.

EXAMPLE 25

The following procedure illustrates a test procedure for the compounds hereof.

Normal female (Sprague-Dawley) rats of 150 to 200 grams each are passively sensitized intradermally by injection of rat anti-egg albumin reaginic sera. After 24 hours, each rat is challenged intravenously with 1 ml. of 0.5% Evans blue, 1 mg. egg albumin plus 0.20 mg. of 6-methylsulfinylxanthone-2-carboxylic acid. Control rats receive no 6-methylsulfinylxanthone-2-carboxylic acid. The dermal bluing is recorded 15 to 25 minutes later. The rats which receive the 6-methylsulfinylxanthone-2-carboxylic acid exhibit a 100 percent inhibition of allergic reaction whereas the control rats exhibit no inhibition.

The above procedure is repeated using 6-methylsulfonylxanthone-2-carboxylic acid, with similar results. The above procedure is repeated using oral administration, with similar results.

The C-6 substituted xanthone-2-carboxylic acid compounds are administered by gavage at a dose of 5 mg. per animal 15 minutes prior to challenge. Twenty to thirty minutes after challenge the degree of dermal bluing is read, with similar results.

Inhibition of reaginic antigen-antibody reactions in rats is regarded as representative of inhibition of human reaginic antigen-antibody reaction which occur during allergic episodes.

Subjects challenged by antigen inhalation are measured for the extent of provoked degree of asthma condition by changes in airway resistance on expiration. The subject compounds are administered as an aerosol by inhalation before antigen challenge. Prevention of asthmatic conditions upon the administration of the compounds is evidenced by a decrease in airway resistance and other, subjective improvements, e.g. reduced cough.

What is claimed is:

1. A method for inhibiting the symptoms of the asthmatic condition resulting from an antigen-antibody reaction in a host susceptible to said reaction which comprises administering to said host an effective amount of from about 0.005 to about 100 mg. per kg. of body weight per day sufficient to produce said inhibition of a compound represented by the formula:

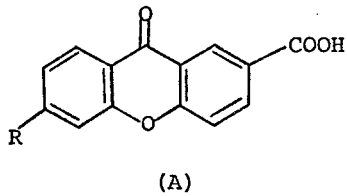

(A)

wherein R is the group

wherein $R^2$ is hydrogen; lower alkyl; cycloaklyl; or halomethyl; or a pharmaceutically acceptable nontoxic alkyl or glycerol ester, unsubstituted, monoalkyl, dialkyl, dialkylaminoalkyl, alkoxyalkyl or phenethyl substituted amide or salt thereof wherein said alkyl and alkoxy groups each contain 1 to 8 carbon atoms.

2. The method according to claim 1 wherein the compound is the compound in which $R^2$ is lower alkyl.

3. The method according to claim 1 wherein the compound is 6-acetylxanthone-2-carboxylic acid.

4. The method according to claim 1 wherein the compound is 6-cyclopropylcarbonyl-xanthone-2-carboxylic acid.

* * * * *